United States Patent [19]

Hartz

[11] Patent Number: 4,777,930
[45] Date of Patent: Oct. 18, 1988

[54] DISPOSABLE HEAT STORAGE UNIT

[76] Inventor: Marvin E. Hartz, 39 Stanley Dr., Glastonbury, Conn. 06033

[21] Appl. No.: 837,760

[22] Filed: Mar. 10, 1986

[51] Int. Cl.$^4$ ............................ A47G 23/04; F24H 7/00
[52] U.S. Cl. ..................................... 126/246; 126/204; 126/400; 62/530; 426/530
[58] Field of Search ................ 62/530; 126/204, 246, 126/273.5, 375, 400; 206/205, 541, 542, 545; 426/109

[56] References Cited

U.S. PATENT DOCUMENTS

| | | | | |
|---|---|---|---|---|
| 2,515,298 | 7/1950 | Feldman | ............................ | 126/204 |
| 3,536,058 | 10/1970 | Hearst et al. | ..................... | 126/204 |
| 3,780,537 | 12/1973 | Spencer | ............................ | 62/530 |
| 4,246,884 | 1/1981 | Vandas | ............................ | 126/246 |
| 4,248,291 | 2/1981 | Jarmul | ................................ | 165/4 |
| 4,498,312 | 2/1985 | Schlosser | ......................... | 62/457 |
| 4,579,170 | 4/1986 | Moses et al. | ................. | 165/104.17 |
| 4,672,178 | 6/1987 | Wada et al. | ......................... | 219/378 |

FOREIGN PATENT DOCUMENTS 57-104052  6/1982  Japan ................................. 126/400

*Primary Examiner*—Samuel Scott
*Assistant Examiner*—Allen J. Flanigan
*Attorney, Agent, or Firm*—Learman & McCulloch

[57] ABSTRACT

A disposable heat storage unit comprises a hermetically sealed, heat conductive pouch containing a quantity of a latent heat substance which may be preheated to an initial temperature higher than that of its heat of fusion so that, upon cooling, it releases first its sensible heat followed by the release of the heat of fusion at a constant temperature over a sustained period of time. The unit may be placed in a container within which is positioned an article whose temperature is to be maintained at an elevated level.

15 Claims, 1 Drawing Sheet

U.S. Patent
Oct. 18, 1988
4,777,930
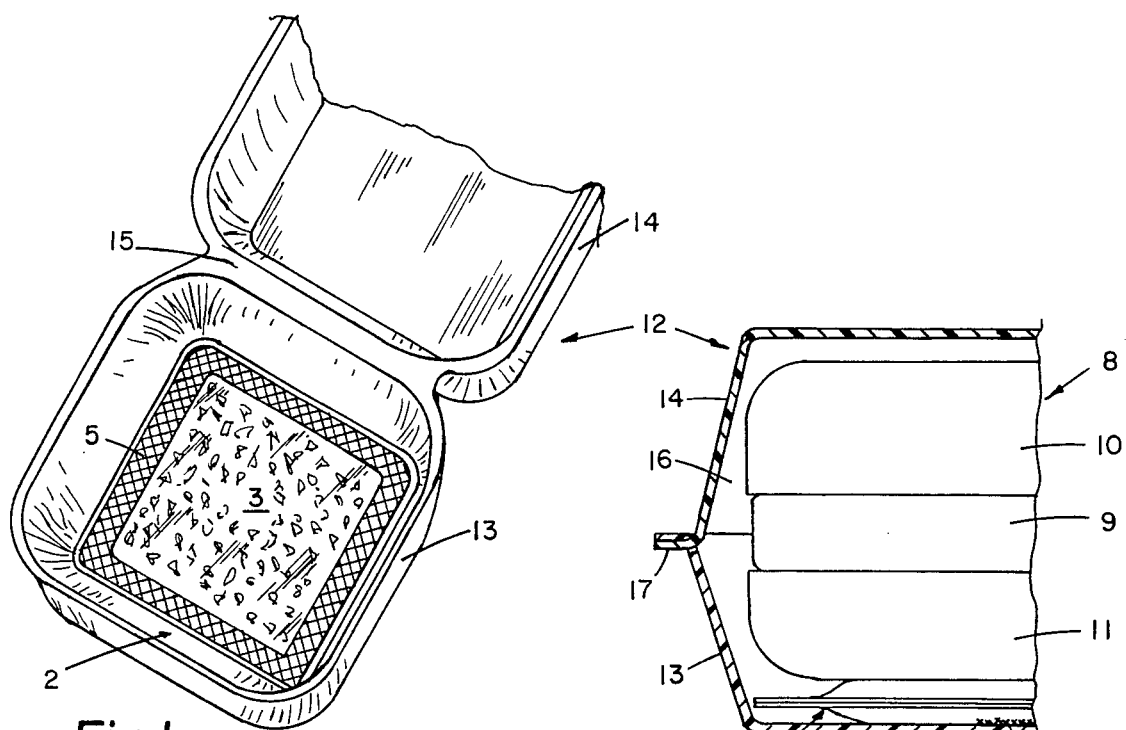
Fig.1
Fig.2
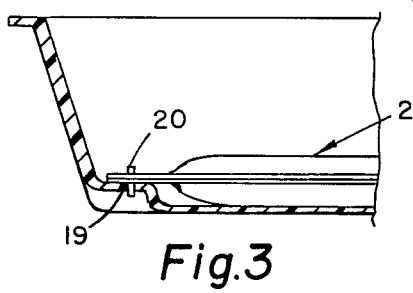
Fig.3
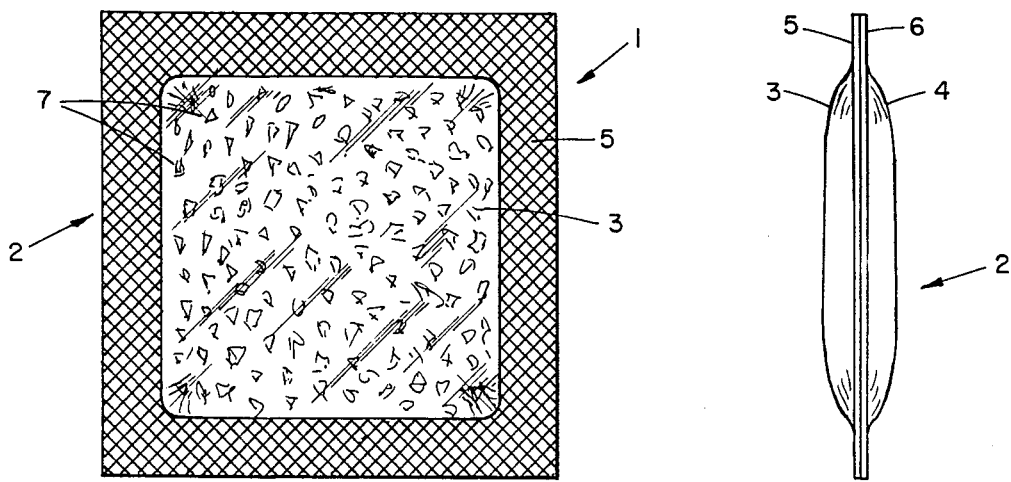
Fig.4
Fig.5

DISPOSABLE HEAT STORAGE UNIT

This invention relates to a disposable heat storage unit of the kind comprising a latent heat substance positioned within a thermal transfer pouch and which emits heat at a substantially constant temperature as the substance cools from an elevated temperature.

BACKGROUND OF THE INVENTION

There are many instances in which an inexpensive, portable, disposable heat source is advantageous. For example, such a heat source advantageously could be used to maintain the warmth of packaged food, such as a hamburger sandwich, thereby enhancing the flavor and appearance of the sandwich especially in those instances in which a period of time is required to transport the sandwich from its production site to its consumption site. Such a heat source also can be used to apply heat to a localized area of the surface of a member that is to be heated for one reason or another, such as to accelerate or effect the curing of an adhesive or the like. Such a heat source also may be used as a therapeutic device for the alleviation of pain accompanying sprains, muscular spasms, and the like.

SUMMARY OF THE INVENTION

A disposable heat source according to the invention comprises a sealed pouch formed of flexible, heat transmitting material containing a latent heat or phase change substance having a high heat of fusion per unit of weight and volume, a high specific heat, and which is non-toxic, inexpensive, and compatible with and inert to the material from which the pouch is formed. The pouch material may constitute any one of a number of metallic foils or heat resistant polymer films capable of withstanding a temperature above that of the heat of fusion of the phase change substance.

The invention also contemplates the combination of such a heat source located within a container adapted for the accommodation of a heated food product whose temperature is to be maintained for a selected period of time at a level above ambient temperature.

Typical latent heat substances appropriate for use include hydrated salts, paraffins, and non-paraffin organic compounds, such as lauric acid, napthalene, glycols, and the like. Typical pouch materials include aluminum foil, heat resistant polyester film, paper/polymer laminates, and other moisture resistant polymer films.

The phase change substance should be one which is inert, non-toxic, inexpensive, and readily available in commercial quantities. It also should be available in dry flake or granular form so as to facilitate automated production of the finished product.

A pouch containing the latent heat substance may be heated to an initial temperature higher that the heat of fusion temperature of such substance and applied either to the member or placed in the receptacle with which it is to be used. The initial temperature, although higher than the heat of fusion temperature, is lower than the melting temperature of the material of the member or receptacle with which the pouch is used.

THE DRAWINGS

Apparatus constructed in accordance with a preferred embodiment of the invention is disclosed in the accompanying drawings, wherein:

FIG. 1 is a fragmentary, isometric view of a sandwich container fitted with a disposable latent heat storage unit according to the invention;

FIG. 2 is an enlarged, fragmentary, vertical sectional view through a container of the type shown in FIG. 1 and within which is a sandwich and a disposable latent heat storage unit;

FIG. 3 is a view similar to FIG. 2, but omitting the sandwich and the upper portion of the container and illustrating an alternate manner of securing the latent heat storage unit to the container;

FIG. 4 is an enlarged plan view of the latent heat storage unit; and

FIG. 5 is an end elevation of such unit.

DETAILED DESCRIPTION

A disposable heat source unit according to a preferred embodiment of the invention is designated generally by the reference character 1 and comprises a hermetically sealed pouch 2 formed of two sheets 3 and 4 of pliable, flexible material sealed to one another along their marginal edges 5 and 6, respectively, but being otherwise unsecured to one another so as to form a receptacle or chamber for the accommodation of a phase change substance 7 having a high heat of fusion per unit of weight and volume and a high specific heat. The phase change substance must be compatible with and inert to the material of which the pouch 2 is formed, as well as having other properties which will be referred to subsequently.

Typical materials which may be used for formation of the pouch 2 include aluminum foil, polyester film, laminations of polymer film and paper, and moisture resistant films.

There are many substances which may be used as the phase change material 7. For example such substance may be selected from paraffins, hydrated salts such as $Na_2SO_4$, $10H_2O$; $Na_2HPO_4$, $12H_2O$; $CaCl_2$, $6H_2O$; $[Na_2CO_3]_2$, $10H_2O$; $Mg[NO_3]_2$, $6H_2O$; $MgCl_2$, $6H_2O$; $MgSO_4$, $12\ H_2O$; and glycols such as polyethylene glycol, but such substance must be chemically inert with respect to the material forming the pouch. Such substance preferably should be non-flammable at the temperatures utilized, inexpensive, readily available in flake or granular form, as well as harmless to humans and the environment. A substance which conforms to all of these parameters is $MgCl_2$, $6H_2O$ having a phase change temperature of 117° C. The phase change temperatures of the other substances may be obtained from tables.

In the production of the heat storage unit 1 the pouch 2 is sealed along three of its marginal sides, leaving one side open through which a quantity of the substance 7 may flow or otherwise be introduced into the chamber following which the fourth marginal edge of the pouch may be closed so as to form a hermetically sealed chamber. The heat storage unit 1 then may be heated to an initial temperature above the heat of fusion of the substance 7, but less than that of the melting point of the material from which the pouch 2 is made. As the temperature of the substance 7 rises above that of the heat of fusion, the substance will change from solid to liquid state. As the substance 7 cools, it will release its sensible heat until it reaches its heat of fusion temperature. Thereafter, it will release its latent heat at a constant temperature corresponding to the temperature of the heat of fusion for the time it takes for all of the substance to revert to its solid state.

It is preferred to fill only a portion, i.e., between about 50% and 90%, of the maximum volume of the chamber. This will enable the pouch to present a fairly flat profile for accommodation in a conventional container without modification thereof. There thus will be a quantity of air within the chamber that may effect oxidation of the substance 7. Since the unit 1 is intended to be used once and then discarded, oxidation is not a problem.

The disposable heat storage unit 1 has a variety of uses. For example, a unit heated to a temperature above that of the heat of fusion of the substance 7 may be applied directly to a surface of a plastic, metal, or other member that is to be heated locally so as to condition a localized zone for reforming or other treatment. The unit 1 also may be used for application to some portion of a person's body for alleviation of the pain arising from strains, sprains, muscle spasms, muscle stiffness, and the like. In the event of use of the unit 1 for such latter purposes, it is contemplated that the unit will be confined within a padded receptacle to protect the person against being burned.

To ensure that the heat storage unit may be used with a variety of differently shaped objects, the material of the pouch and the substance 7 should be of sufficient pliability or deformability as to ensure conformation to the geometry of the object to be heated, not only at the temperature of the heat of fusion of the substance 7, but also at the higher initial temperature to which the pouch and its contents may be heated.

It also is anticipated that a heat storage unit constructed in accordance with the invention may be used to minimize the heat loss from a heated article of food such as a cooked hamburger sandwich 8 having a meat patty 9 sandwiched between two halves 10 and 11 of a bun. Such a sandwich commonly is placed, while the patty is hot, in a container 12 having lower and upper halves 13 and 14 joined to one another by a hinge 15. The two halves 13 and 14 may be arranged in overlying relation, as indicated in FIG. 2, so as to form a compartment 16 within which the sandwich 8 is accommodated. Suitable fastening means 17 commonly are associated with the container halves to prevent inadvertent opening of the compartment. Conventionally, the material from which the container 12 is made comprises a foamed, thermally insulating plastic such as polystyrene, or paper, paperboard, or papier-mache.

In the embodiment illustrated in FIG. 2 the pouch 2 is secured to the inside surface of the bottom of the lower half 13 of the container by a suitable adhesive 18. In the embodiment shown in FIG. 3, however, the pouch 2 is secured to a portion 19 of the bottom wall of the lower container by a metal staple 20. Other means may be used to secure the pouch within the container, but it also is possible simply to lay the pouch on the bottom of the lower half on the container 12 and thereby dispense with any additional securing means.

The size of the pouch 2 and the quantity of phase change substance 7 contained therein may vary according to the size of the article whose heat is to be maintained and the container therefor.

As has been indicated, the materials comprising the heat source unit 1 must be compatible with one another and inert to the container and its contents. Further if the heat source unit is to be sufficiently economical to be disposable, the materials incorporated in the unit must be readily available in commercial quantities, inexpensive, and susceptible to automatic production procedures. Aluminum foil, polyester film, polymer coated paper, and $MgCl_2$, $6H_2O$ in flake or granular form satisfy these requirements.

EXAMPLE

A hermetically sealed pouch 2 measuring 7.6 cm $\times$ 7.6 cm $\times$ 0.9 cm formed of aluminum foil and having a foil weight of 5.45 g, and containing 19.8 g of flake form $MgCl_2$, $6H_2O$ was placed in the bottom of a foamed polystyrene container having tapered side walls and flat top and bottom walls of about 16 mm thickness. The overall dimensions of the container were 11.4 cm $\times$ 11.4 cm $\times$ 6 cm and it had an internal volume of about 780 cc. A hamburger meat patty having an uncooked weight of about 114 g and a cooked, internal temperature of 62.8° C. was placed in a 25 g bun having a temperature of 22.2° C., which also was the ambient temperature. Prior to placement of the pouch in the container it was heated to a temperature of 135° C. by immersing it in cooking oil at that temperature. An identical sandwich was placed in an identical container under the same temperature conditions, but without the presence of the heated pouch therein. At the end of fifteen minutes, all of the phase change substance had returned to its solid state and the temperature of each of the two meat patties was measured. The temperature of the patty in the container without the heat source was 51° C., whereas the temperature of the patty in the container having the heat source was 59.4° C.

Not only was the meat patty of the sandwich taken from the container utilizing the heat source warmer than that of the other sandwich, but so was the bun. Thus, the sandwich taken from the container employing the heat source was considered more savory than the other.

The disclosed embodiments are representative of preferred forms of the invention, but are intended to be illustrative rather then definitive thereof. The invention is defined in the claims.

I claim:

1. A single use, disposable, heat storage unit comprising a sealed pouch forming a wholly internal, sealed chamber having a predetermined maximum volume; and a particulate, fluent, dry, latent heat storage substance within said chamber, the volume of said substance within said chamber being sufficiently less than said predetermined maximum volume that the particles of said substance do not fill said chamber and are freely movable in all directions within said chamber, said substance having a predetermined heat of fusion temperature in excess of 100° C., said pouch being formed of pliable, moisture resistant, thermal transfer material capable of withstanding without adverse consequences being heated to an initial temperature higher than the heat of fusion temperature of said substance.

2. A unit according to claim 1 wherein said material and said substance are sufficiently pliable at said initial temperature to conform to the shape of a surface to which said pouch may be applied.

3. A unit according to claim 1 wherein said material comprises a metallic foil.

4. A unit according to claim 1 wherein said material comprises a heat resistant polymer.

5. A unit according to claim 1 wherein said material comprises a paper/polymer laminate.

6. A unit according to claim 1 wherein said substance comprises a temperature responsive phase change material selected from the class consisting essentially of salt hydrates, paraffins, and glycols.

7. A unit according to claim 1 wherein said substance is hexahydrated magnesium chloride.

8. A unit according to claim 1 wherein said substance is non-toxic and inert to said material.

9. A unit according to claim 1 wherein said substance occupies between about 50% and about 90% of the maximum volume of said chamber.

10. Thermal heat storage apparatus comprising a disposable container having walls of thermally insulating material forming a compartment; a single use, disposable, sealed, flexible pouch positioned within said compartment and formed of moisture resistant, heat transfer material, said pouch forming a wholly internal, sealed chamber having a maximum volume; a dry, particulate, fluent, latent head storage substance accommodated in said chamber, the volume of said substance within said chamber being sufficiently less than said maximum volume that the particles of said substance do not fill said chamber and are freely movable in all directions within said chamber, said substance having a heat of fusion temperature in excess of 100° C., the material of said wall and the material of said pouch being capable of withstanding without adverse consequences being heated to an initial temperature in excess of the heat of fusion temperature of said substance.

11. Apparatus according to claim 10 wherein said compartment has a bottom and wherein said pouch is supported on said bottom.

12. Apparatus according to claim 10 including means securing said pouch to one of said walls of said compartment.

13. Apparatus according to claim 12 wherein said securing means comprises an adhesive.

14. Apparatus according to claim 12 wherein said securing means comprises a fastener extending through said pouch and into said one of said walls.

15. A device according to claim 10 wherein said substance occupies between about 50 and 90 percent of the maximum volume of said chamber.

* * * * *

UNITED STATES PATENT AND TRADEMARK OFFICE
CERTIFICATE OF CORRECTION

PATENT NO. : 4,777,930
DATED : October 18, 1988
INVENTOR(S) : Marvin E. Hartz

It is certified that error appears in the above-identified patent and that said Letters Patent is hereby corrected as shown below:

Column 5, line 17, change "head" to -- heat --.

Column 6, line 3, change "wall" to -- walls --.

Signed and Sealed this

Seventh Day of February, 1989

Attest:

DONALD J. QUIGG

*Attesting Officer*  *Commissioner of Patents and Trademarks*